(12) United States Patent
Vlaskin

(10) Patent No.: US 10,266,960 B2
(45) Date of Patent: Apr. 23, 2019

(54) METHOD AND PRECURSOR FOR LARGE SCALE SYNTHESIS, GROWTH AND MODIFICATION OF UPCONVERTING NANOCRYSTALS DERIVED FROM A NAYF₄ HOST

(71) Applicant: Excelsior Nanotech Corporation, Bellevue, WA (US)

(72) Inventor: Vladimir Vlaskin, Mill Creek, WA (US)

(*) Notice: Subject to any disclaimer, the term of this patent is extended or adjusted under 35 U.S.C. 154(b) by 110 days.

(21) Appl. No.: 15/159,684

(22) Filed: May 19, 2016

(65) Prior Publication Data

US 2016/0340793 A1    Nov. 24, 2016

Related U.S. Application Data

(60) Provisional application No. 62/165,651, filed on May 22, 2015.

(51) Int. Cl.
| C30B 7/14 | (2006.01) |
| C30B 29/12 | (2006.01) |
| C01F 17/00 | (2006.01) |
| C07F 5/00 | (2006.01) |

(52) U.S. Cl.
CPC ............ C30B 7/14 (2013.01); C01F 17/0031 (2013.01); C07F 5/00 (2013.01); C30B 29/12 (2013.01)

(58) Field of Classification Search
CPC .................................. C30B 29/12; C30B 7/14
See application file for complete search history.

(56) References Cited

U.S. PATENT DOCUMENTS

| 3,083,143 A | 3/1963 | Schmid | |
| 2011/0033368 A1* | 2/2011 | Ye | B82Y 30/00 423/509 |
| 2011/0127445 A1 | 6/2011 | Zhang | |
| 2013/0287703 A1 | 10/2013 | Jang | |
| 2013/0302358 A1 | 11/2013 | Collins | |
| 2014/0227548 A1 | 8/2014 | Myrick | |
| 2015/0362432 A1* | 12/2015 | Han | C09K 11/02 435/4 |
| 2016/0168459 A1* | 6/2016 | Cohen | C09K 11/7773 428/402 |

FOREIGN PATENT DOCUMENTS

CN    103911143 A  *  7/2014  ............. C09K 11/02

OTHER PUBLICATIONS

European Patent Office, English computer translation of CN103911143A (2018).*
Nakamura, International Preliminary Report on Patentability, Received in PCT/US2016/033454, dated Nov. 28, 2017.
Fedorov, "Nanofluorides", Journal of Fluorine Chemistry [on-line], Jun. 25, 2011, vol. 132, pp. 1012-1039.

* cited by examiner

*Primary Examiner* — Matthew J Song
(74) *Attorney, Agent, or Firm* — Glenn H. Lenzen; Dietze and Davis, P.C.

(57) ABSTRACT

A method and a precursor for the large-scale production of upconverting nanocrystals derived from a NaYF₄ host are provided. A rare earth based precursor is combined with a hydrophobic fluoride precursor, which is based upon a long-chain n-alkyl amine to form a reaction solution. The reaction solution is heated under an inert gas to temperatures above 300° C., whereby upconverting NaYF₄-based nanocrystals are nucleated and grown.

11 Claims, 2 Drawing Sheets

METHOD AND PRECURSOR FOR LARGE SCALE SYNTHESIS, GROWTH AND MODIFICATION OF UPCONVERTING NANOCRYSTALS DERIVED FROM A NAYF$_4$ HOST

PRIORITY TO RELATED PATENT APPLICATIONS

This application is a U.S. patent application which claims the benefit of U.S. Provisional patent application Ser. No. 62/165,651 filed on May 22, 2015, which is incorporated herein by reference.

FIELD OF THE INVENTION

The present invention relates to the synthesis of nanocrystals. More specifically, the present invention relates to an inexpensive, large scale, environmentally safe production method and precursor for the high temperature synthesis, growth and modification of sodium yttrium tetra-fluoride (NaYF$_4$) nanocrystals.

BACKGROUND OF THE INVENTION

The use of nanocrystals, also referred to as nanoparticles, in both research and commercial applications is growing dramatically. Their diverse optical, chemical and electrical properties make them attractive for use in many applications such as in semiconductor devices, photodetectors, lasers, medical imaging and pathogen detection systems and materials processing methodologies and associated systems. The various applications in which nanocrystals may be used depend in no small measure upon the nanocrystal composition, associated physical properties, compatibility with other materials and ease of synthesis. For example, nanoparticle shape may be controlled by varying the ratios of the host crystal and various solvents, surfactants, monomer concentrations and other constituents involved in the synthesis process. Temperature control is also an important variable in end product quality and performance.

High temperatures are generally necessary for the production of high quality nanocrystals of various chemical compositions. The large selection of high boiling point hydrophobic solvents makes the availability of hydrophobic precursors for the particular kind of nanocrystal, essential. As a classic example, the problem of making a hydrophobic selenide precursor for the high temperature preparation of CdSe nanocrystals has been solved with the use of tri-alkyl phosphine ligands. These readily convert elemental selenium into the selenide anion form and bring it into the hydrophobic reaction solution. As an example, U.S. Pat. No. 7,998,271 B2, issued Aug. 16, 2011, to Alkhawaldeh et al., ("the '271 patent") describes a synthesis of CdSe nanocrystals that uses trioctylphoshine to render the selenide anion soluble in the hydrophobic reaction environment. However, the '271 patent does not address the above-referenced problems associated with the production of NaYF$_4$ nanocrystals on a commercially viable basis.

A variety of potential new technologies are based upon upconverting nanocrystals, the best performing of which are based upon a NaYF$_4$ host. Synthetic procedures for NaYF$_4$ nanocrystal production have gradually improved over the last decade. The nanocrystals produced by the latest methods exhibit narrow size distributions and high upconversion efficiencies; however, the necessity to use volatile components presents a significant challenge for inexpensive large scale manufacture of these nanocrystals.

Prior to the publication of the synthetic procedure based on NH$_4$F dissolved in methanol and/or water in 2008, precursors such as NaF and CF$_3$COOH have been used as the fluoride source. (Zhengquan Li and Yong Zhang. Nanotechnology, 2008, 19, 345606). More recently, a novel procedure has been reported that utilizes NaYF$_4$ nanocrystals of a less stable, cubic, crystal structure as a precursor for the more stable, hexagonal, NaYF$_4$ nanocrystals. (Noah J. J. Johnson, et.al. J. Am. Chem. Soc. 2012, 134, 11068-11071). These and similar methods have been adapted by the majority of laboratories in academia and have generated the highest quality NaYF$_4$ nanocrystals to date but are not feasible for large-scale commercial production environments.

A notable attempt to remove volatile components from the reaction solution was reported in 2009 by Liu C. et al. published a report in the Journal of Materials Chemistry. Their method allowed for the production of very monodisperse nanocrystals of NaYF$_4$ doped with various rare earth cations. The critical weakness of their approach was the necessity to use excess fluoride precursor to control growth, which stemmed from the low solubility of NaF in the organic solution that lacked a hydrophobic component that could bind fluoride. The extra fluoride ions that are not bound to 3+ cations are free to react with anything in the reaction solution, including the glassware and solvent. An attempt to follow this approach on an industrial scale would carry great risks including, but not limited to fires and release of deadly toxic fumes.

Moreover, the strategy based on organic phosphines that has been successful for CdSe has not been reported in conjunction with and is unlikely to be feasible for the preparation of NaYF$_4$, especially on a large scale. By-products that can potentially form during the course of a high temperature reaction involving fluoride and organic phosphines are closely related to nerve agents such as Sarin. Consequently, development of the analogous hydrophobic precursor for the preparation of NaYF$_4$ nanocrystals requires the identification of new ligands that both solubilize fluoride and do not inhibit the growth of high quality crystals.

Possession of a hydrophobic precursor not only simplifies preparation of a batch of nanocrystals, but also simplifies its modification. Deposition of a "shell" of a given composition onto upconverting NaYF$_4$ nanocrystals is a very popular method for improving their optical properties. Adoption of such a method for large scale manufacture in the absence of a hydrophobic precursor is limited by the necessity to cycle the reaction temperature between two different temperature thresholds (one being less than 100° C. and a second being greater than 300° C.) with every new addition of volatile precursors. Such manipulations become progressively more time consuming and expensive as the scale of the process is increased.

In view of the foregoing, it will be apparent to those skilled in the art that a need exists for an improved and simplified process and associated materials for mass production of high quality upconverting nanocrystals, in particular, nanocrystals based upon a NaYF$_4$ host, without the use of volatile solvents and the formation of undesirable and hazardous toxic side products.

SUMMARY OF THE INVENTION

In an embodiment, a precursor and manufacturing process of the present invention addresses the aforementioned problems associated with the prior art by providing a hydrophobic precursor appropriate for the addition of a fluoride anion during the growth of $NaYF_4$ nanocrystals.

In another embodiment, high temperature methods are provided for both growth and/or modification of $NaYF_4$ nanocrystals that circumvent the use of a volatile solvent and instead rely on a novel fluoride bearing precursor based on long-chain n-alkyl amines.

These and other objects and features of the present invention will be apparent from the accompanying drawings, description of the invention and supplemental supporting materials provided herein.

DETAILED DESCRIPTION OF THE INVENTION

It should be noted that the present description is by way of illustration only, and that the concepts and examples presented herein are not limited to use or application with any single method for the large scale synthesis, growth and modification of upconverting nanocrystals or any precursor associated therewith. Hence, while the details of the synthesis method and its components described herein are for the convenience of illustration and explanation with respect to the exemplary embodiments, the principles disclosed may be applied to other types of upconverting nanocrystal synthesis, growth and modification methods without departing from the scope of the present invention.

Figure 1:
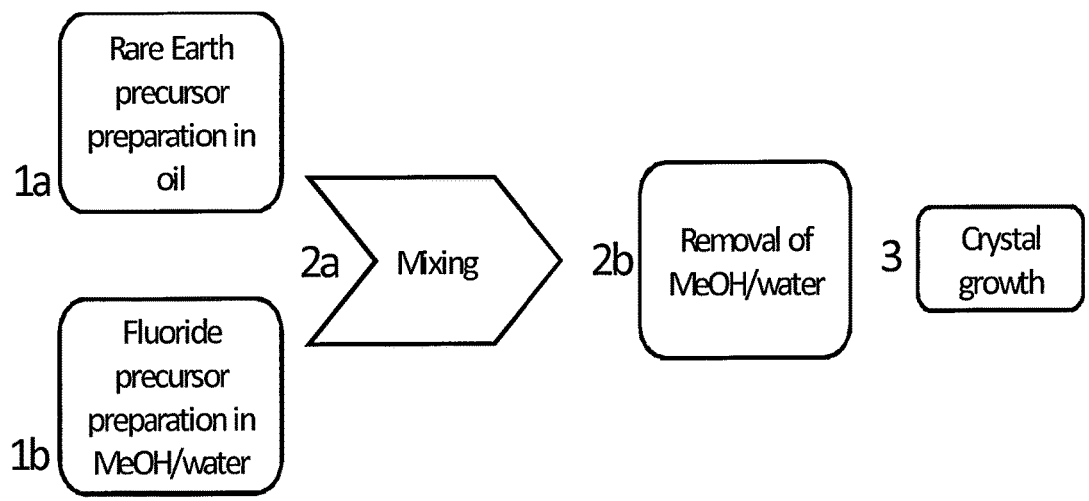
FIG. 1 is a flow chart of the standard prior art procedure for the production of a $NaYF_4$ nanocrystal.

Referring now to FIG. 1, a flow chart of a conventional prior art process for the preparation and growth of a rare earth-based nanocrystal is illustrated schematically. Initial steps as shown in blocks 1a and 1b respectively involve the preparation of a rare earth or cationic precursor and a fluoride precursor, The rare earth precursor is formed by first placing rare earth salts into a solution containing oleic acid, a fatty acid that occurs naturally in various animal and vegetable fats and oils and which in appearance is an odorless, colorless or yellowish oil. The solution is then heated under vacuum at a temperature below 100° C.

Preparation of the fluoride precursor involves dissolving $NH_4F$ in a solution of methanol (MeOH), sodium hydroxide (NaOH) and water, as illustrated as step 1b in FIG. 1. The two precursors are then combined and mixed in step 2a of FIG. 1.

Next in the sequence is removal of MeOH and water, a critical step, which involves slow and attentive heating of the reaction solution under vacuum, whereby the volatile parts are transferred into a cold trap. This step is depicted schematically in FIG. 1, block 2b. The inadvertent introduction of excessive heat and/or vacuum during this step will result in the transfer of not only the volatile parts, but also a portion of the reaction solution to the cold trap, as well. Transfer of the reaction solution to the cold trap results in undesirable deposition of it onto the adjacent equipment used in the process. Typically, the production of one gram of crystal product requires the removal of 50 mL of methanol.

Crystal growth, shown in the reaction process sequence at FIG. 1, block 3, begins once the reaction is placed under an inert gas and taken to a high temperature, i.e., greater than 200° C. In the event that the processes described in step 2 outlined above are not completed, the reaction solution will deposit itself all over the equipment used to introduce the inert gas.

Figure 2:
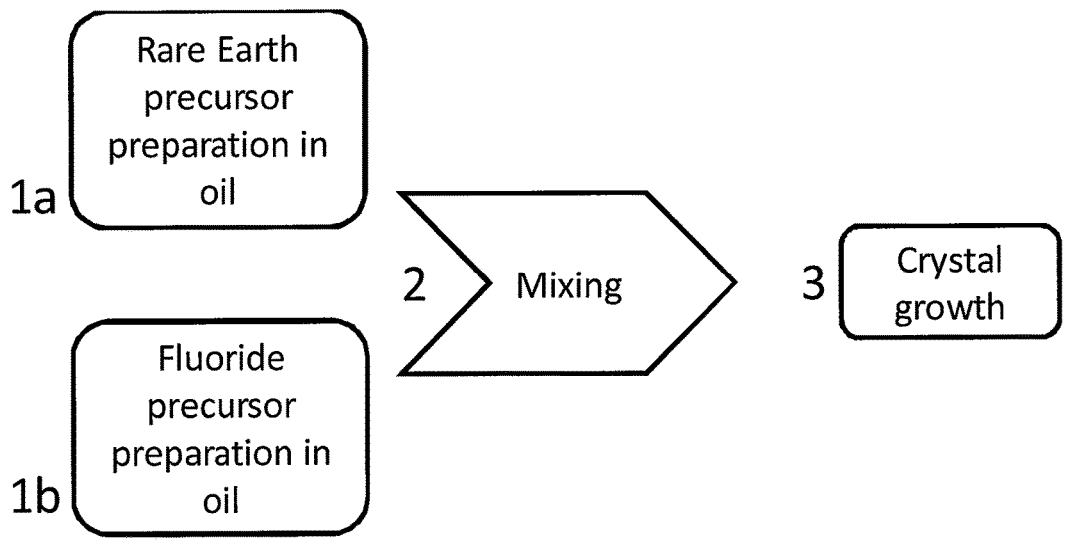
FIG. 2 is a flow chart of the procedure for the production of a $NaYF_4$ nanocrystal in accordance with an embodiment of the present invention.

Referring now to FIG. 2, a flow chart illustrates graphically the steps of the new and novel process and precursor of the instant invention which overcome the shortcomings of the aforementioned prior art attempts to synthesize nanocrystals on a mass produced scale. As shown schematically in FIG. 2, block 1a, preparation of the rare earth or cationic precursor proceeds in accordance with published syntheses known in the art. As described above, this process involves placing a preselected amount of rare earth salts into a solution containing a preselected amount of oleic acid and a solvent and heating the solution under vacuum below 100° C.

FIG. 2, block 1b. depicts figuratively the step of preparation of a hydrophobic fluoride precursor in accordance with the present invention. This step involves dissolving a preselected amount of $NH_4F$ in a solution that contains preselected amounts of sodium oleate and an amine, such as, by way of illustration and not of limitation, hexadecylamine or cetylamine hydrofluoride. It is to be understood, however, that a wide range of hydrophobic amines, such as amines having a variable carbon chain length of eight (8) to eighteen (18) carbon atoms. In addition, secondary amines and tertiary amines, such as dioctylamine and trioctylamine have demonstrated excellent results in the novel process of the instant invention and may also be used without departing from the scope thereof. As shown in FIG. 2, block 2, the rare earth precursor and the fluoride precursor solutions prepared in accordance with the above steps are then transferred to a separate reaction vessel and mixed to form a precursor mixture, which contains nutrients for the crystallization and growth of nanoparticles. A brief vacuum is then applied to remove any oxygen that entered the system during the transfer. Thereafter, the precursor solution mixture is placed under an inert gas and heated to a temperature greater than 200° C. As in the case of the occurrence of an incomplete step 2 described above in the prior art process, an incomplete step 2 in the process of the instant invention will likewise result in the reaction solution being deposited all over the equipment used to introduce the inert gas.

Figure 3:
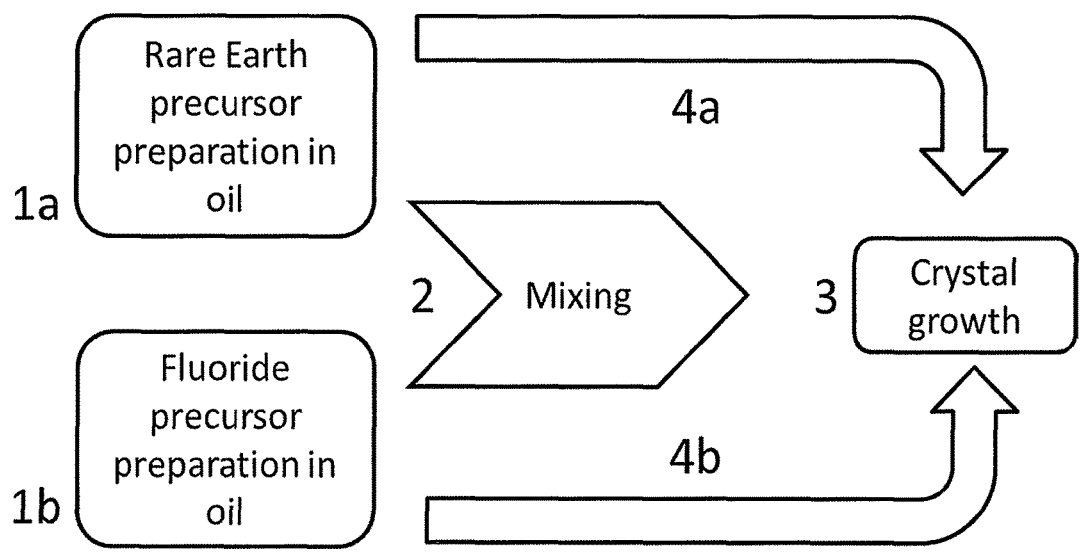
FIG. 3 is a flow chart for the production and modification of a $NaYF_4$ nanocrystal in accordance with another embodiment of the present invention

Referring now to step 3 of FIG. 2. and FIG. 3., crystal growth occurs above 300° C., as small nucleates of the thermodynamically stable hexagonal crystal phase increase in size by depleting the precursor mixture of nutrients and cannibalizing any unstable cubic crystal phase particles formed at lower temperatures.

The crystal growth of step 3, either terminates once all of the nutrients are depleted or is prolonged by the addition of fresh precursors from steps 1a and 1b. The latter case is depicted in FIG. 3 as steps 4a and 4b, respectively, and these steps may be repeated on a continuing basis, thereby sustaining the large-scale production of the nanocrystals.

Nanoparticles grown from multiple nutrient additions are referred to as "core/shell" nanoparticles. This "core/shell" motif presents a strategy for segregating specific active rare earth cations either at the surface or near the center of each nanoparticle. Such segregations can be used to amplify direct energy transfer to species at the surface or to prevent non-radiative losses, increasing the optical quantum yield, respectively. The instant invention allows the preparation of the "core/shell" motif within an uninterrupted step 3. Unlike the novel process of the present invention, prior art methods that rely on the aqueous precursor require the reaction temperature to be brought under 100° C. followed by the reproduction of steps 2a and 2b of FIG. 1.

The ability to continuously deliver precursors using steps 4a and 4b of FIG. 3 in accordance with the present invention allows the implementation of the seeded growth approach, which is particularly attractive for large scale production. Given the possession of 1 g of highly uniform 10 nm average diameter particles, it is possible to convert these into 1 kG of 100 nm average diameter particles following only steps 4a and 4b of the method of the present invention as shown in the process flow diagram of FIG. 3, repeatedly.

In accordance with the methodologies herein described, employing a hydrophobic precursor removes one of the biggest challenges concerning the problem of scaling the synthesis and distillation of $NaYF_4$ nanocrystals for mass production. The difficulty in preparing such a precursor has to do with the high reactivity of the fluoride ion. The key element of the present invention is the realization that the standard precursors used in the preparation of $NaYF_4$ nanocrystals may act as proton scavengers, thereby minimizing the likelihood of the creation of hydrogen fluoride and promoting the production of ammonia gas that can be easily removed under vacuum. The volatility of ammonia allows for the accelerated conversion of $NH_4F$ into cetylamine hydrofluoride by mass action, applying a dynamic vacuum through a cold trap to convert it into a solid.

EXAMPLES

Accordingly, the following materials and equipment were used to synthesize $NaYF_4$ based upconverting nanocrystals in accordance with the procedures outlined above and set forth in greater detail below:

A. Chemical Compounds: 1-octadecene (ODE), hexadecylamine (HDA), sodium oleate (NaOA), ammonium fluoride ($NH_4F$), yttrium oleate (YOA). A variety of amines may be used in place of HDA in order to meet the solubility and/or boiling point constraints posed by a particular procedure.

B. Equipment: Round bottom glass flask, vacuum and inert gas capable Schlenk line, heating mantle, stirring apparatus, and a thermometer.

C. Procedure:

1. Preparation of the Fluoride Precursor:

A solution containing 120 g of ODE and 35 g of sodium oleate was degassed under vacuum above 100° C. To this solution, 40 g of HDA was added and degassed under vacuum above the melting point of HDA. Against the flow of an inert gas, 6 g of $NH_4F$ powder was added into the solution while the solution was still liquid. Vacuum and heat were carefully applied until no more bubbles evolved from the solution.

2. Preparation of the Rare Earth/Cationic Precursor:

A solution of 200 g of ODE, 200 g of oleic acid and 12 g of rare earth acetate salts were placed under vacuum and were brought to 100° C. over the course of 1 hour. The amount of applied heat and vacuum are controlled to keep the evolution of water and acetic acid gases at a steady rate. The preparation of the precursor is complete once all of the solids are dissolved and no more gases are evolved.

3. Combination of the Fluoride and the Cationic Rare Earth Precursors:

To a degassed solution containing YOA in ODE, the fluoride containing solution (above) was added while still liquid, with care taken to exclude oxygen from the system.

4. Use in Various $NaYF_4$ Nanocrystals Syntheses:

The solution containing the fluoride precursor and the necessary cations was slowly added to a solution containing preformed nanocrystals to induce their ripening at reaction temperatures between 200° and 400° C. Alternatively the solution can be used to nucleate nanocrystals by raising its temperature above 300° C. Using the aforementioned components, precursor and procedures, uniform nanocrystals (confirmed by transmission electron microscopy), which exhibit bright upconversion luminescence have been produced.

Changes may be made in the above methods, compounds, devices and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, device and structure, which, as a matter of language, might be said to fall there between.

What is claimed is:

1. A method for the large scale, environmentally safe preparation of rare earth-based nanocrystals, the method comprising;

preparing a rare earth precursor solution including the steps of heating a solution of preselected amounts of oleic acid and yttrium oleate (YOA) under a vacuum to a temperature which is less than 100° C.;

preparing a hydrophobic fluoride precursor solution comprising preselected amounts of $NH_4F$, sodium oleate (NaOA) and a hydrophobic amine having a variable carbon chain length of between eight (8) to eighteen (18) carbon atoms in a first reaction vessel;

degassing the hydrophobic amine/NaOA solution under vacuum at a temperature above 100° C.;

adding to the hydrophobic amine/NaOA solution a preselected amount of hexadecylamine (HDA);

degassing the hydrophobic amine/NaOA/HDA solution under vacuum above the melting point of HDA;

introducing an inert gas to the first reaction vessel;

adding a preselected amount of $NH_4F$ in powder form to the hydrophobic amine/NaOA/HDA solution;

applying a vacuum and heat at a preselected temperature to the hydrophobic amine/NaOA/HDA solution until it is completely degassed;

adding the degassed and heated hydrophobic amine/NaOA/HDA solution to a solution of preformed $NaYF_4$ nanocrystals to form a mixture;

transferring the rare earth precursor and the hydrophobic fluoride precursor solutions to a second reaction vessel;

mixing the rare earth precursor and the hydrophobic fluoride solutions in the reaction vessel whereby a reaction mixture is formed, the reaction mixture containing nutrients adapted to cooperate with one another to crystallize and grow nanocrystals;

applying a vacuum to the reaction mixture, whereby any oxygen which may have been introduced during the mixing step is removed;

introducing an inert gas to the reaction vessel; and heating the mixture to a reaction temperature in the range of approximately 200° C. to approximately 400° C., whereby ripening of the preformed nanocrystals is induced.

2. The method of claim 1 wherein the hydrophobic amine comprises a secondary amine.

3. The method of claim 2 wherein the secondary amine comprises dioctylamine.

4. The method of claim 1 wherein the hydrophobic amine comprises a tertiary amine.

5. The method of claim 4 wherein the tertiary amine comprises trioctylamine.

6. The method of claim 1 wherein the hydrophobic amine is selected from the group consisting essentially of hexadecylamine, octadecylamine and oleylamine.

7. The method of claim 1 wherein the hydrophobic amine comprises cetylamine hydrofluoride.

8. The method of claim 1 further including the step of heating the mixture to a reaction temperature comprises heating the mixture to a temperature of approximately 300° C., until the nutrients in the reaction mixture are depleted.

9. The method of claim 8 further including the steps of adding fresh rare earth precursor solution and fresh hydrophobic precursor solution to the reaction vessel.

10. The method of claim 9 wherein the steps of adding fresh rare earth precursor solution and fresh hydrophobic precursor solution to the reaction vessel are repeated on a continuing basis, whereby large scale, environmentally safe preparation of rare earth-based nanocrystals is sustained.

11. The method of claim 1 wherein the hydrophobic amine comprises 1-octadecene (ODE).

\* \* \* \* \*